United States Patent [19]

Kulbe et al.

[11] Patent Number: 4,689,322

[45] Date of Patent: Aug. 25, 1987

[54] PHARMACEUTICAL PRODUCTS, CALCIUM MIXED SALTS OF POLYMERIC, ANIONIC CARBOXYLIC ACIDS AND/OR THEIR ESTERS OF SULFURIC ACID, AND METHODS FOR THEIR PREPARATION AND USE

[75] Inventors: Klaus D. Kulbe, Gartringen; Hans Weber, Ludwigsburg, both of Fed. Rep. of Germany

[73] Assignee: Algina Aktiengesellschaft, Zug, Switzerland

[21] Appl. No.: 696,632

[22] Filed: Jan. 30, 1985

Related U.S. Application Data

[63] Continuation-in-part of Ser. No. 516,787, Jul. 25, 1983, abandoned.

[30] Foreign Application Priority Data

Jul. 28, 1982 [DE] Fed. Rep. of Germany ....... 3228321

[51] Int. Cl.$^4$ ................ A61K 31/715; A61K 31/735; C08B 37/04; C08B 37/06
[52] U.S. Cl. .......................... 514/54; 536/2; 536/3; 536/121
[58] Field of Search ................. 514/54, 891; 424/37; 536/121, 114, 2, 3

[56] References Cited

U.S. PATENT DOCUMENTS

| | | | |
|---|---|---|---|
| 2,543,699 | 2/1951 | LeGloahec | 536/121 |
| 2,572,923 | 10/1951 | Gaver et al. | 536/121 |
| 2,871,236 | 1/1959 | Bryant | 536/121 |
| 3,326,755 | 6/1967 | Sheth | 514/54 |
| 3,362,951 | 1/1968 | Farkas et al. | 536/121 |
| 3,579,634 | 5/1971 | Brown | 514/54 |
| 3,678,149 | 7/1972 | Prigal | 514/54 |
| 3,712,883 | 1/1973 | Nordgren | 536/114 |
| 4,125,608 | 11/1978 | Blum et al. | 514/54 |
| 4,140,760 | 2/1979 | Withington | 514/54 |
| 4,520,017 | 5/1985 | Tunc | 514/54 |

FOREIGN PATENT DOCUMENTS

| | | | |
|---|---|---|---|
| 6649M | 3/1969 | France . | |
| 0038722 | 3/1982 | Japan | 514/54 |
| 1212896 | 11/1970 | United Kingdom . | |

OTHER PUBLICATIONS

CA 80:6974U Jan. 14, 1974.
CA 80:55759M Mar. 18, 1974.
CA 80:11559S Jan. 21, 1974.
CA 53:19223 Oct. 25, 1959.
CA 97:108515P Sep. 27, 1982.

*Primary Examiner*—Ronald W. Griffin
*Attorney, Agent, or Firm*—Walter H. Schneider

[57] ABSTRACT

A pharmaceutical product is disclosed which contains at least a calcium salt or a calcium mixed salt of a natural or chemically modified polymeric, anionic carboxylic acid and/or an ester of sulfuric acid, and additive materials and/or an ester of sulfuric acid, and additive materials and/or carrier materials. There are further disclosed calcium salts, and methods of preparation thereof, comprised of polymannuronic acid, polygalacturonic acid, polyglucuronic acid, polyguluronic acid, the oxidation products of homoglycans, the oxidation products of heteroglycans, or their mixtures, for controlling the levels of phosphate, calcium and iron in patients with chronic uraemia and/or the control of the oxalate and/or phosphate of the blood in kidney stone prophylaxis.

12 Claims, 7 Drawing Figures

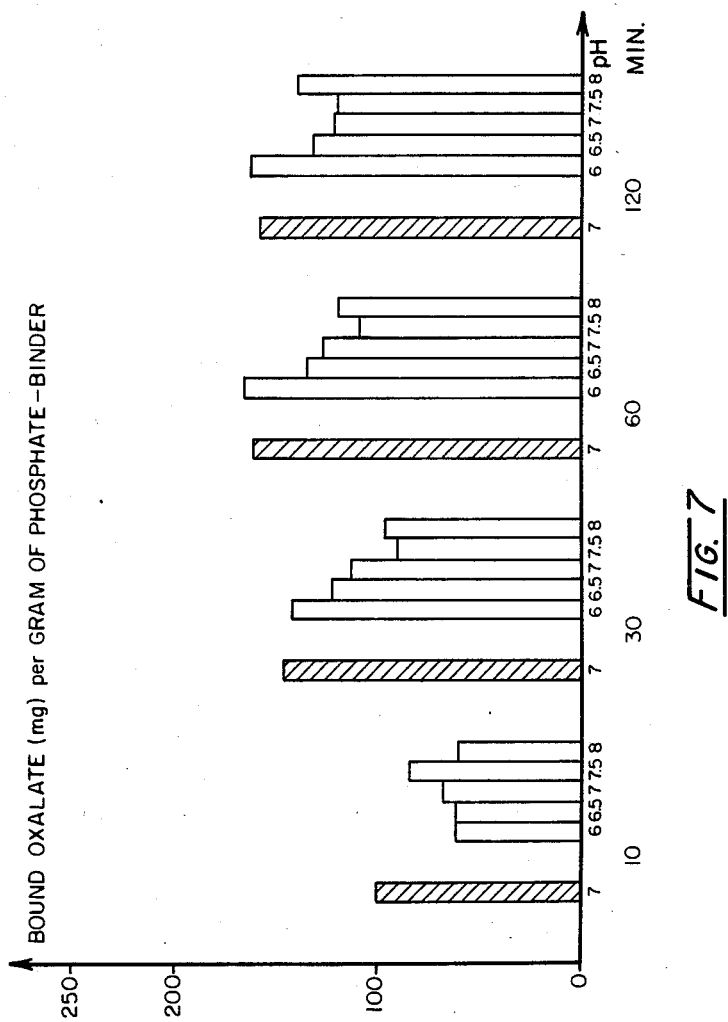

4,689,322

PHARMACEUTICAL PRODUCTS, CALCIUM MIXED SALTS OF POLYMERIC, ANIONIC CARBOXYLIC ACIDS AND/OR THEIR ESTERS OF SULFURIC ACID, AND METHODS FOR THEIR PREPARATION AND USE

CROSS REFERENCE TO RELATED APPLICATION

This application is a continuation-in-part of copending application Ser. No. 516,787, filed July 25, 1983, now abandoned.

BACKGROUND OF THE INVENTION

1. Field of the Invention

The present invention relates to pharmaceutical products which are particularly useful in the treatment of hyperphosphateaemia at chronic uraemia, as well as for the prophylaxis of kidney stones, particularly oxalate stones, to calcium mixed salts of polymeric, natural and chemically modified anionic carboxylic acids and/or esters of sulfuric acid, to methods for their preparation, and to methods of their use.

At the present time, there are approximately 14.000 patients in the Federal Republic of Germany which suffer from chronic uraemia, and the tendency is increasing. These patients have to undergo a blood purification or cleansing treatment for three to six hours three times per week. Such known treatments include haemodialysis or haemofiltration, and peritoneal dialysis, respectively. These treatments aim to remove uraemic toxins, such as, for example, urea, uric acid, creatinine and the like, as well as phosphate, from the organism, i.e. from the blood. Despite of dietary measures, the phosphate level is still too high in most patients even after the blood purification. The hyperphosphateaemia represents a substantial factor in the pathogenesis of the secondary hyperparathyrodism with development of the renal osteopathy under chronic dialysis treatment. The causes of this are the binding of phosphate to certain proteins and the intestinal resorption of phosphate from food and of phosphate from the fluid of the gall. Accordingly, almost all uraemia patients have to rely on additional medication to lower the phosphate level to the normal range.

2. Description of the Prior Art

Aluminium hydroxides were predominantly used in the last few years for the intestinal binding of phosphate in such patients. These include, for example, ALUDROX ®, ANTIPHOSPHAT ®, ALUCAP ®, and PHOSPHONORM ®. These were applied in amounts of up to 10 g and more per day (M. B. Kaye, Arch. Intern. Med., 124,646 (1969)). A further aluminium-containing salt for the reduction of the phosphate resorption is described in DE-OS No. 2 618 083 (DE-OS=German patent publication).

However, these known products for the binding of phosphate have disadvantages. Through partial dissolution of the aluminium hydroxide, Al $(OH)_3$, in the stomach to Al $(OH)$ $Cl_2$ and $AlCl_3$, $Al^{3+}$ is liberated, and this is partially resorbed in the stomach and the upper small intestine, enters, via the blood, into the bone substance as well as other parts of the body (liver, erythrocytes, etc.), and, in the case of many years of exposure thereto, causes considerable damage (compare, for example, haemodialysis-encephalopathy, osteomalacia with tendency to spontaneous fractures, hypercalcaemia, decreasing of muscle strength) (A. C. Alfrey, J. M. Mishell, J. Burks, S. R. Contiguglia, H. Rudolph, E. Lewin, J. H. Holmes, Trans. Amer. Soc. Artif. Int. Org., 18, 257 (1972); A. C. Alfrey, G. R. Le Gendere, W. D. Kaehny, New. Eng. J. Med., 294, 184 (1976); A. M. Pierides, W. G. Edwards jr., U. X. Cullum jr., J. T. Mc Call, H. A. Ellis, Kidney Intern., 18, 115, (1980)). According to EDTA-statistics 10 to 12% of the dialysis patients die annually with cerebral incidents, more than a few due to a dialysis-encephalopathy (H. Pogglitsch, Nieren-u. Hochdruck-krankheiten (Kidney and High Pressure Diseases), 10, 210 (1981)).

The lowering of the average dose of aluminium hydroxide to a third thereof caused a significant lowering of the concentrations of plasma-aluminium. Thus, from a medicinal point of view it appears urgently adviseable to discontinue the presently used aluminium preparations for the binding of phosphate. However, till now no suitable therapeutical replacement has been available.

From the food there are resorbed, per day, approx. 200 g water and 2.7 g phosphate in the intestine. From digestive fluids are added a further 8.000 g water and 0.3 g phosphate. The resorption of $Ca^{2+}$ and $Fe^{2+}$ occurs in the upper small intestine and the middle intestine, respectively.

Because of disturbances of the functioning of the kidneys during chronic uraemia, the following amounts of substances have to be removed from the blood of a patient, per treatment, generally three times per week, among others: 3 to 6 g phosphate and 1.500 to 2.000 g water.

The manifestation of uraemia includes furthermore a deficiency of $Ca^{2+}$ and $Fe^{2+}$ ions. Thus, such a patient should be given approx. 1 g calcium and 100 to 200 mg $Fe^{2+}$, per day. The latter is only resorbed to 10 to 15%. Of disadvantage is a momentary excess dose during the short period of administering the entire amount, as well as a related incompatibility (danger of hypercalcaemia). Furthermore, most of the patients who suffer from chronic uraemia also suffer from sluggishness of the bowel and constipation of the bowel, respectively. Such patients frequently exhibit a deficiency in trace elements.

A composition for raising the calcium content of blood in animals is described in DE-OS No. 2 505 755 (DE-OS=German patent publication), as well as a method of preparing such composition. The composition is comprised of an aqueous mixture of calcium chloride and a gel-forming polymer. As polymers, the polyvinyl alcohols or polyethylene glycols, acrylic acid polymer and carboxymethylcellulose, are described in the prior art patent publication. These compositions can not be used in humans, because until now it is not proven that they per se, their monomers, or their metabolism products, respectively, are not toxic.

Kidney stones, particularly oxalate stones, can be formed, among others, thereby that through the intake of food which is rich in oxalate, and by resorption of the oxalate in the intestine during urine preparation, there arise high concentrations of oxalate in the kidney, and the solubility product of the calcium oxalate is exceeded. Similar considerations apply in the formation of calcium-phosphate stones.

SUMMARY OF THE INVENTION

It is an object of the present invention to provide a pharmaceutical product which is capable of removing phosphate from the small intestine, particularly in patients with chronic uraemia.

It is also an object of the invention to provide a pharmaceutical product which is adapted to regulate the levels of calcium and iron in the blood, and which is adapted to supply, as required, to the patient further trace elements.

In accordance with yet another object of the invention there is to be provided a pharmaceutical product which prevents the formation of kidney stones. The product is particularly intended for patients who are known to be susceptible to formation of kidney stones.

It is also an object of the present invention to provide calcium mixed salts, as well as methods of preparing such salts, which can be used for the binding of phosphate, for the partial removal of water, and for the replenishing of the $Ca^{2+}$ and $Fe^{2+}$ requirements, as well as the requirements for trace elements.

The pharmaceutical products according to the present invention are to be adapted not to liberate $Al^{3+}$, either in the small intestine or in the stomach, they are not to cause harmful side effects, and the basic substance thereof is to be adapted to be prepared in a simple manner.

In accordance with one aspect of the invention there is provided a pharmaceutical product which contains at least one calcium salt or one calcium mixed salt of a natural or chemically modified polymeric, anionic carboxylic acid and/or one of its esters of sulfuric acid, whereby the calcium salt contains of from 0.5 to 5 times the stoichiometrically required amount of calcium ions; the cations in the calcium mixed salt are selected from the group consisting of calcium, iron and/or cations of trace elements; the sum of the cations in the calcium mixed salt is in the range of from 0.5 to 5 times the stoichiometrically required amount; further contains 0.45 to 4.95 times the stoichiometrically required amount of calcium ions and 0.05 to 2.5 times the stoichiometrically required amount of iron ions and/or cations of trace elements; and further contains the usual addition materials and/or carrier materials.

In accordance with a further aspect of the invention there is provided a calcium mixed salt which comprises the salt of a polymannuronic acid, polygalacturonic acid, polygulcuronic acid, polygurulonic acid, an oxidation product of homoglycans or heteroglycans or their esters of sulfuric acid, or mixtures of these compounds, with the cations being selected from the group consisting of calcium, iron and/or cations of trace elements, whereby the sum of the cations is in the range of from 0.5 to 5 times the stoichiometrically required amount; and it comprises 0.45 to 4.95 times the stoichiometrically required amount of calcium ions and 0.05 to 2.5 times the stoichiometrically required amount of iron ions and/or other ions of trace elements. In accordance with a preferred embodiment, the amount of iron and/or cations of trace elements is of from 0.1 to 2 times the stoichiometrically required amount. Still further preferred is the range of from 0.2 to 1.5 times the stoichiometrically required amount, and particularly preferred is the range of from 0.3 to 0.6 times the stoichiometrically required amount.

In accordance with a further aspect of the invention there is provided a method of preparing the calcium mixed salt, which method comprises the steps of: adding, to a 2 to 20% aqueous solution of a polycarboxylic acid solution from the group consisting of polymannuronic acid, polygalacturonic acid, polyglucuronic acid, polygurulonic acid, the oxidation products of homoglycans, the oxidation products of heteroglycans or their esters of sulfuric acid or their mixtures, an alkali hydroxide, to a pH value of from 5.0 to 8.0; agitating the solution, as required, at room temperature for 1 to 2 hours; drop-wise adding the resultant solution at a temperature in the range of from 0° to 50° C. into a 0.2 to 2M solution of a physiological acceptable calcium salt having a pH value which was adjusted to the range of from 2 to 8 by the addition of alkali hydroxide; or adding the resultant solution drop-wise into a 0.01 to 1M aqueous solution of a physiologically acceptable iron-II-salt; and/or, as required, into a 0.01 to 0.5M aqueous solution of physiologically acceptable salts of trace elements; whereby calcium ions in a concentration of from 0.01 to 2M can be added to this solution; maintaining the mixture at a temperature of from 2° to 50° C. for a period of time of from 1 to 20 hours; filtering the reaction product; washing the resultant precipitate to obtain the required final content of free (trace-) ions; and drying the precipitate.

In accordance with yet another aspect of the present invention there is provided a method of use of the calcium salts of polymannuronic acid, polygalacturonic acid, polyglucuronic acid, polyguluronic acid, the oxidation products of heteroglycans or their esters of sulfuric acid or their mixtures, for controlling the phosphate or calcium level in patients with chronic uraemia and/or for controlling the oxalate and phosphate level in the prophylaxis of kidney stones, comprising the step of administering a therapeutically effective amount of said salt.

In accordance with yet another aspect of the present invention there is provided a method of use of the calcium mixed salts for the control of the phosphate or calcium or iron level in patients with chronic uraemia and/or for controlling the oxalate and phosphate level in the prophylaxis of kidney stones, comprising the step of administering a therapeutically effective amount of said mixed salt.

In accordance with the present invention the following advantages can be achieved:

(1) Liberation of $Al^{3+}$ does not occur in a natural way (as from $Al(OH)_3$ in the stomach and small intestine, or from $AlPO_4$ already formed in the small intestine, when using the presently available binders of phosphate).

(2) No depletion of phosphate as is the case with $Al(OH)_3$ medication is observed.

(3) The basic substances are, as alginic acid, pectic acid and others, of plant origin and they are allowed as addition materials under applicable regulations concerning food. They do not release damaging monomers, as is possibly the case, for example, with fully synthetic or possibly semi-synthetic ion exchange resins.

(4) The substances are present in the small intestine as gels and are, as well as the released polymers (for example, pectic acid) and their monomeric component units, such as mannuronic acid, galacturonic acid, etc., fully biologically decomposable by the microorganisms in the intestine.

(5) The requirement for calcium alginate is relatively low, for example, between from 2 to 30 g for the removal of 5 g phosphate. Furthermore, an excess of the fully, or partially, dried agent can be administered for swelling purposes.

(6) The consistency of the gel can be predetermined and varied over a wide range in conformity with the starting components. Thus, for the administration, for example as lyophilisate, the susceptibility of calcium can be influenced and thereby also the reaction rate, or velocity, of formation of hydroxylapatite, and possibly resorption of additional $Ca^{2+}$ or $Fe^{2+}$ ions. In the case of low concentrations of calcium in the starting reaction, softer gels are obtained.

(7) A doping with desired ions, such as $Ca^{2+}$ and $Fe^{2+}$, can be carried out over a wide range already during the preparation of the gel, and by suitable washing methods. Losses of calcium and magnesium as in the case of $Al(OH)_3$ medication do not arise but a patient with uraemia can be supplied with lacking ions through the new method.

(8) The consistency of gels, in which 50% of the $Ca^{2+}$ is replaced by $Fe^{2+}$, corresponds to that of pure calcium alginate gels.

(9) The material of the gel is stable in the absence of phosphate or oxalate under physiological pH conditions.

(10) Because of the slow dissolution of the gel in the presence of phosphate, and the immediate formation of hydroxylapatite (HAP)—$Ca_{10}(PO_4)_6(OH)_2$— also at a doping of the gel with an excess of calcium, the danger of hypercalcaemia is prevented. The latter was observed at administration of calcium in the form of $CaCl_2$ (acid), Ca-lactate, $CaCO_3$ (basic, $CO_2$ development), and Ca-acetate.

(11) When the form of the gel is appropriately selected, one can expect, after an initial phase, a uniform formation of hydroxylapatite and Ca-resorption. In the case of gels with an excess of Ca, a partial precipitation of HAP can occur immediately, and the slow gel dissolution serves then for liberation of $Ca^{2+}$ for the desired resorption in a uremic patient.

(12) In the case of gels which have been washed five times, 50% of the available phosphate are already converted (compare FIG. 1). Lyophilisates of this material react even faster, since the structure of the gel is broken, which leads to an easier calcium accessibility. Pulverization would increase this effect. In the preparation of the starting material one can, however, optimize the appropriate reaction rate, or velocity, for a material which is too lyophilizing.

(13) Precipitated HAP is removed with the bowel content, and this applies analogously to oxalate as calcium oxalate. In the case of low pH values in the lower portion of the large intestine and rectum, there can arise a partial dissolution of HAP, however, neither $Ca^{2+}$ nor phosphate are resorbed in this portion of the intestine.

(14) Also in the presence of phosphate a partial separation of sulfate is possible, despite of low solubility of the HAP.

(15) The forms of administration can include: gel, partially or fully dried gel (beads) and lyophilisate (in powder form, as required). For the prevention of the intake of water from the stomach by way of swelling, a coating resistant to the stomach fluids would be necessary. For intestinal phosphate binding and treatment of hyperphosphatemia using the presently preferred calcium salt, calcium alginate, a relatively large amount, namely about 5 g–15 g of the calcium alginate will generally be used, about 5 g–10 g being preferred. Such relatively large amounts may lead to problems with patients compliance, particularly in dialysis patients since these patients have to take the phospahte binder over long periods of time. Calcium alginate in the form of powder, tablets, granulates and hard gelatin capsules can be taken by the patients. However, there may arise problems with the drug compliance of the patients. It has been found that calcium alginate, when embodied in soft gelatine capsules, may be administered in relatively high amounts without the patient having difficulties in swallowing the preparation. By incorporating the calcium alginate in soft gelatin capsules which comprise, in addition to calcium alginate, either a hydrophobic filler (e.g., medium chain triglycerides together with lecithin) or hydrophilic material (e.g., polyethylenglycol), capsules which contain up to about 1.2 g of calcium alginate can be prepared which present no problems of patient compliance. Use of such a hydrophobic or hydrophilic filling material is, therefore, very desirable since one can thereby conveniently form soft gelatin capsules which contain relatively high amounts of calcium alginate but which can still be swallowed relatively easily. Preferred soft gelatin capsules contain about 0.5 to 1.2 grams of calcium alginate. Preparation of soft gelatin capsules is accomplished by using conventional methods well known to those skilled in the art.

(16) On administration of a dried calcium alginate gel or calcium pectate gel, the use of a swelling substance is possible (5 to 10 g $H_2O$/g dry form).

(17) The $Ca^{2+}$, liberated in the presence of, for example, sodium phosphate, from the gel, reacts preferentially with oxalate ions to form substantially insolube calcium oxalate, and in this manner prevents tthe resorption of oxalate from the intestine into the blood. The accompanying reduced concentration of oxalate of the blood leads to a considerable reduction and prevention, respectively of the existing danger of formation of oxalate stones during the formation of final urine, due to the concentration process in the kidney, and the resultant exceeding of the solubility product of Ca-oxalate.

In accordance with the present invention the calcium salts of natural or chemically modified polymeric, anionic carboxylic acids or esters of sulfuric acid are used. Such natural polymeric, anionic carboxylic acids, as they are used in accordance with the invention, are, in many cases, ion exchangers which form gels with $Ca^{2+}$. In accordance with one aspect of the invention, combinations of the following groups A, B and C can be used:

(A) Polyuronides and related substances with relatively large parts of uronic acids, such as, for example, glucuronic acid, galacturonic acid, mannoronic acid, and iduronic acid. The naturally occuring alginic acids, containing of from 0 to 100% mannuronic acid and of from 0 to 70% guluronic acid, can also be used. Particularly suitable are:

1. Polymannuronic acid, such as, for example, alginic acid. In accordance with the present invention, alginic acid is used with particular preference.

2. Polygalacturonic acid, such as, for example, pectic acid, or pectins having low methanol esterification.

3. Polyglucuronic acid, for example, such as, prepared from cellulose by way of microbial oxidation.

4. Polyguluronic acid, for example, certain alginic acids.

Of course, mixtures of the foregoing polyuronides can be used.

(B) Oxidation products of homoglycans such as, for example argaroses, dextrans, celluloses, pullulans, and the like.

(C) Oxidation products of heteroglycans:

1. Galactomannans (guar gum=guaran; carboxyguar gum) (carob-gum=locust bean gum=carob bean flour).
2. Sulfate-esterified carrageens (kappa, i).
3. Glucomannans.

As well, mixtures of these compounds can be used.

(D) Mixtures of the substances enumerated under (A) to (C) above.

Several structural formulae of these compounds are presented in the following:

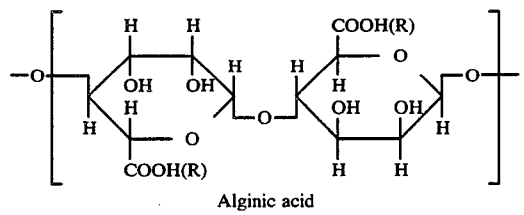
Alginic acid

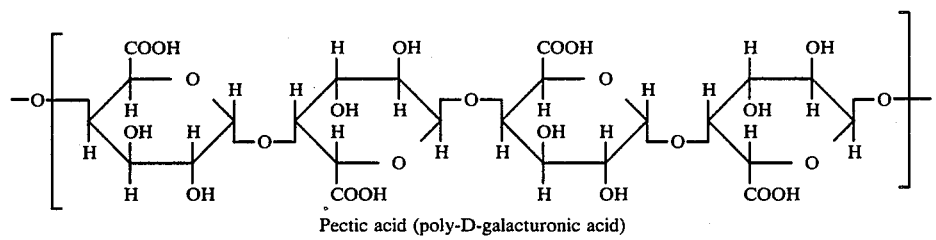
Pectic acid (poly-D-galacturonic acid)

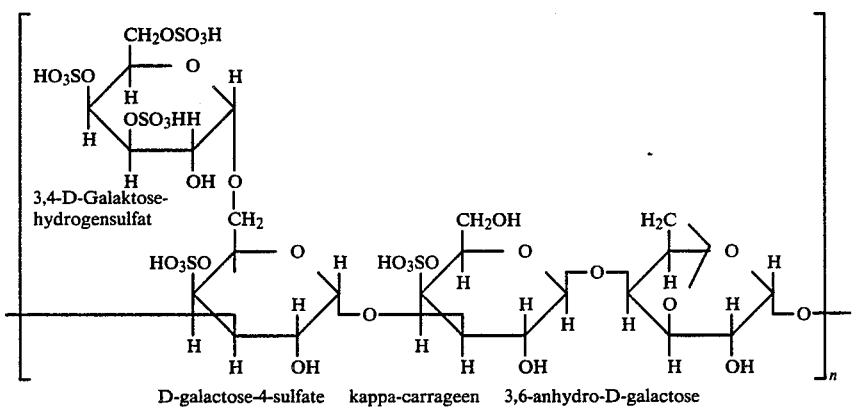
3,4-D-Galaktose-hydrogensulfat   D-galactose-4-sulfate   kappa-carrageen   3,6-anhydro-D-galactose

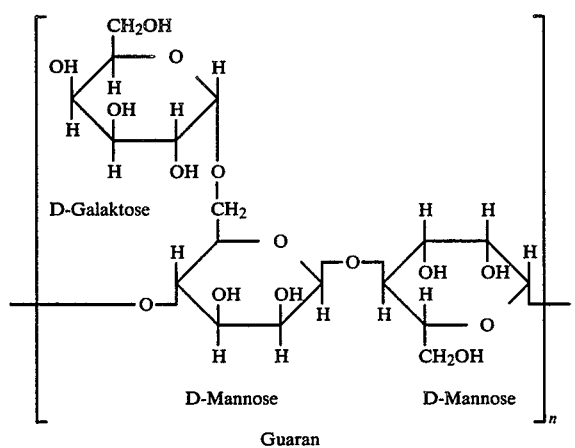
D-Galaktose   D-Mannose   D-Mannose
Guaran

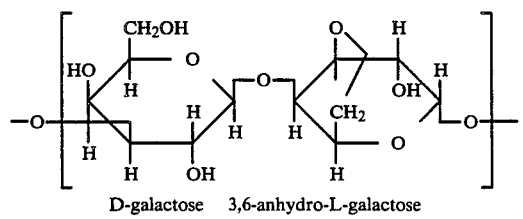
D-galactose   3,6-anhydro-L-galactose

-continued
Agar-Agar

The oxidation of the compounds of the groups (B) and (C), is known and has been described in the literature (P. Nuhn, Chemie der Naturstoffe-(Chemistry of the Natural Substances), Akademie-Verlag, Berlin (1981), page 166–167)). Aldoses, particularly in polymers, can be carefully oxidized without separation of C—C bonds, for example, by oxygen, in the presence of platinum, permanganate, or nitrogen dioxide, at their terminal free, primary, hydroxyl groups, whereby the corresponding uronic acids (carboxyl functions) are formed, provided the terminal position was not participating in the formation of the glycan. The required protection of the aldehyde function (anomeric center) for monosaccharides is usually provided in the case of polymeric sugars up to the terminal units. Epimerisation at C-5 is easily achieved in the case of hexoses.

Polysaccharides are used preferably in the method of the present invention. These belong to the class of the carbohydrates and comprise highly molecular compounds, made of glycosidically interconnected units of monosaccharide. Polysaccharides tend to form highly viscous solutions with water, or gels in the presence of $Ca^{2+}$ and other ions, and are of use as thickening or gel agents for foodstuffs, as well as carrier and encapsulating materials for medications in the pharmaceutical industries. Such polysaccharides are particularly well suited for the present invention, and in the following several substances which are particularly preferred, are described in greater detail (compare also the contribution "Polysaccharides" in Enzyklopädie Naturwissenschaft und Technik (Encyclopedia of Natural Sciences and Technology), published by Verlag Moderne Industrie, Landsberg/Lech (1980)).

Alginic Acid and its Salts

Polymerisate from D-mannuronic acid, L-guluronic acid; $\beta$-1, 4-glycosidically interconnected; molecular weight 12.000 to 200.000 Daltons; source: brown algae; easily digestible, up to 1.000 COOH groups in the molecule.

Alginic acid and its salts were up to now used in the production of ice creams, marmalades, fruit jellies, cosmetics, soaps, creams, edible sausage skins, mayonnaises, pudding, prepared soups, soup cubes, and as weight-reducing agents. In accordance with the present invention they are particularly preferred since they comprise nontoxic substances, and there does not exist a concern for their use from the point of view of foodstuff regulations or pharmaceutical regulations. Even erythrocytes can be contained in a functional manner over lengthy periods of time in Ca-alginate gels (G. Pilwat, P. Washausen, J. Klain, U. Zimmermann, Z. Naturforsch. (Journal of Natural Sciences Research), 35c, 352 (1980)).

Alginic acid consists of polymerisates of mannuronic acid and guluronic acid, which condense together to form polymerised blocks of mannuronic acid (MM-blocks), guluronic acid (GG-blocks) or alternating blocks containing manuronic acid and guluronic acid (MG-blocks). The ratio of guluronic acid to manuronic acid has a strong influence on the properties of the alginic acid.

For intestinal phosphate binding and/or for treatment of hyperphosphatemia, calcium salts of alginic acid are preferably used which contain calcium in the range of 0.8 to 1.1 of the stoichiometrically required amount. Such a calcium salt contains, on the one hand, enough calcium to allow a sufficient degree of phosphate binding, and, on the other hand, not sufficient calcium to potentially raise the serum calcium to dangerous levels.

Such calcium alginates preferable contain, on a weight basis, about 8.5 to 11.5% of calcium, based on the weight of the dried calcium alginate.

For intestinal phosphate binding and treatment of hyperphosphatemia, a calcium salt of alginic acid, in which there is a high content of gulurnic acid, is preferred. Such is preferred since it is guluronic acid residues which form salts with calcium ion and since alginic acids containing a high content of guluronic acid, therefore, may contain higher amounts of bound calcium. An alginic acid, which contains 56 to 75% by weight of guluronic acid, and correspondingly 25 to 44% by weight of mannuronic acid, is particularly preferred for preparing the calcium salts. Calcium alginates from such an alginic acid are produced containing calcium in the preferred amount of 0.8 to 1.1 of the stoichiometrically required amount of calcium. The calcium contained in such a calcium alginate is about 8.5 to 11.5% by weight, the preferred range discussed above. The preferred calcium alginate contains about 10% by weight of calcium.

Alginic acid with a high proportion of guluronic acid may be obtained readily from the algae Laminaria hyperborea which grows on the Norwegian coast. Preferably, only the stems and/or the whole plant is used as the source of alginic acid. The leaves alone are not used. Isolation and purification of the alginic acid from the algae is accomplished using conventional methods known to one skilled in the art.

The preferred calcium alginate prepared from alginic acid obtained as described above from Laminaria hyperborea and containing about 10% by weight of calcium binds about 90–130 mg phosphate per gram of calcium alginate when tested in vitro. In clinical application, this calcium alginate provides good phosphate binding, while, at the same time, maintaining stable serum calcium levels.

Pectic Acid and its Salts (Pectates)

Pectic acid is comprised of $\alpha$-1,4-glycosidically interconnected units of galacturonic acid. Approximately 20 to 60% of the acid groups are esterified with methanol in the pectin (salts: pectinates). They have a low content of galactose and arabinose. From these, pectic acid can be obtained by saponification. Citrus-pectin represents pure polygalacturonic acid. The molecular weights are from 30.000 to 500.000 Daltons. Ca-pectate is insoluble in water; pectic acid has a selectivity towards calcium.

Pectinates are used in jellies which are low in sugar, or free of sugar, marmalades, milk puddings, fish and meat in gels or aspic, for maintaining the colour in frozen strawberries, cosmetics, pharmaceuticals, drying agents and protective colloids, additions to ice cream, chewing gum, and in the preparation of spreadable cheese. There does not exist, again, a concern for their use from the point of view of foodstuff regulations or pharmaceutical regulations.

Agarose

Agarose is comprised of alternating units of $\beta$-1,3-linked, or interconnected, D-galactose and $\alpha$-1,4-linked, 3,6-anhydro-L-galactose. A small part of the galactose molecules is methylated at C-6, or esterified with sulfuric acid.

Dextrans

Dextrans represent $\alpha$-1,6 and 1,4 ($\alpha$-1,3) linked polyglucoses, molecular weight up to several million Daltons. Bephadex is a dextran which is three-dimensionally linked to epichlorohydrin. As such, it is indifferent towards anions and cations, gel-former due to numerous OH-groups, used as matrix for functional groups in ion exchangers.

Carrageen (ans)

Carrageenans having a moleculr weight of from 100.000 to 800.000 Dalton are known; approximately 25% sulfate-content; various types: kappa-carrageenan: comprised of alternating 1,3 or 1,6, respectively, linked 3,6-anhydro-$\alpha$-D-galactose and D-galactose-4-sulfate; gel-forming; only partially oxidizable lambda carrageenan: $\alpha$-1,3-glycosidically linked D-galactose-2(4)-sulfate residues and 1,4-linked D-galactose-2,6-disulfate residues and 1,4-linked-D-galactose-2,6-disulfate residues; does not gel; and still partially oxidizable at C-6: i-carrageenan: from D-galactose-4-sulfate formed in 1,3-linkage and 3,6-anhydro-D-galactose-2-sulfate formed in 1,4-linkage; forms gel with $Ca^{2+}$.

Carob Bean Flour (Carobin)/Guar Flour=-Guaran=Guar-gum

Galactomannans. The latter substances are used for emulsifying, thickening and binding of ice creams, soft cheese, bakery goods, and sauces. There are no limits as to quantity with respect to their uses (compare, J. Schormueller, Lehrbuch der Lebensmittelchemie (Textbook of Foodstuff Chemistry), 2nd edition, (1974), page 100–109, 305, Springer Verlag, Berlin, Heidelberg, New York).

The calcium salts or calcium mixed salts of the compounds mentioned in the foregoing can be present either stoichiometrically or non-stoichiometrically. For example, the calcium may be present in the calcium salts in an amount in the range of from 0.5 to 5, preferable of from 0.6 to 2.8, and still more preferable in an amount of from 1 to 2, of the stoichiometrically required amount. Particularly preferable is a 1.5 stoichiometric excess.

It was further found that in calcium salt solutions used for gel hardening (or bead formation), for example, 0.3 to 0.8M, preferably 0.5M calcium salt solutions, of from 0.05 to 0.5M of the calcium ions can be replaced by iron ions and/or other cations, especially cations of trace elements. In other words, the calcium gels can be doped with iron and other cations.

Calcium is present in the calcium mixed salts in an amount which corresponds to 0.45 to 4.95, preferably 0.6 to 2.8, still further preferably 1 to 2, of the stoichiometrically required amount. In the following tables there are shown the respective concentrations of cations in relation to the stoichiometrically required amount.

TABLE I

| | Calcium mixed salts | | |
|---|---|---|---|
| Range | Sum of Cations | Ca Ions | Fe Ions, Trace Elements |
| General | 0.5–5 | 0.45–4.95 | 0.05–2.5 |
| Preferred | 0.8–3 | 0.6–2.8 | 0.2–1.5 |
| Particularly Preferred | 1.3–2.5 | 1–2 | 0.3–0.6 |

As examples there are shown in the following Table II the stoichiometrically required amounts of various metals in relation to alginic acid.

TABLE II

| Stoichiometric Amounts | | |
|---|---|---|
| $Ca^{2+}$ | 104 mg/g | as dry beads |
| $Fe^{3+}$ | 98 mg/g | as dry beads |
| $Fe^{2+}$ | 130 mg/g | as dry beads |
| $Na^+$ | 118 mg/g | as dry beads |
| $K^+$ | 185 mg/g | as dry beads |

Particularly preferred are the following substances:
1. For the Elimination of Phosphate
Ca-alginate
Ca-Fe-alginate
Ca-pectate
Ca-Fe-pectate
Fe(II)-Ca-alginate
Fe(III)-Ca-alginate
2. For the Elimination of Oxalate
Ca-alginate
Ca-pectate In accordance with a particularly preferred embodiment of the invention, the substances mentioned in the foregoing contain from 1 to 2 times the stoichiometrically required amount, and the other ions are present in an amount corresponding to 0.3 to 0.6 of the stoichiometrically required amount.

Particularly preferred substances have the following composition in accordance with the present invention:

| | $Ca^{2+}$ | Fe | $K^+$ | $Na^+$ | $\Sigma$ |
|---|---|---|---|---|---|
| IGB-21 | 160 | — | 8 | 20 | 188 mg/g |
| IGB-27 | 140 | 45 | 8 | 20 | 213 mg/g |

The mixed salts in accordance with this invention can be prepared in a simple manner. The aqueous solution of the polycarboxylic acids or esters of sulfuric acid are used, whereby the aqueous solutions have a concentration of from 2 to 20%, preferably 4 to 12%, and particularly preferred is a concentration of from 6 to 10%. The pH of the solution is adjusted using an alkali hydroxide, for example, sodium hydroxide, to a value of from 5 to 8, preferably to 7.4. The solution of the polycarboxylic acids or of the esters of sulfuric acid can be stirred, as required, at room temperature for 1 to 2 hours. This solution is added, at a temperature of from 0° to 50° C., particularly preferred is a temperature of from 10° to 30° C., to aqueous solutions of calcium salts with concentrations of from 0.2 to 2M, particularly of from 0.3 to 1M, and more particularly preferred, the concentration is 0.5M. The pH of such solutions was adjusted with alkali hydroxide to a value of from 2 to 8. A portion of the calcium ions can be replaced, either in full or in part, by $Fe^{2+}$ or other cations.

The chlorides are preferred for the addition of the various cations because they represent physiological anions which occur, for example, in the blood, and which provide, in the form of hydrochloric acid, the major portion of the acidity of the stomach. On the other hand, other salts of the metals which do not have toxic effects in the body such as, for example, inorganic salts, such as carbonate; or inorganic salts, such as the acetates, ascorbates, citrates, gluconates, lactates, levulinates, malonates, pantothenates, saccharates or tartrates, can be used.

The resultant reaction product, generally obtained in the form of beads, is next filtered, and the desired concentration of free cations is adjusted by means of a washing which is to be standardized in accordance with the individual case at hand. The concentration of cations is complexometrically determined.

The resultant precipitate can be dried after washing. The drying is carried out in accordance with methods such are known per se. The water content in the end product can be in the range of from 0 to 50%.

The resultant product can be prepared, as is known, in the form of pills, dragees, capsules (e.g., hard or soft gelatin capsules or tablets. The dosage to be administered on a daily basis is in the range of from 2 to 30 g dry basis, in conformity with the composition of the gel and the doping, as well as being in conformity with the pH of the intestine section which resorbs the phosphate. The dosage is also dependent on the amount, the composition, and the residence time of the food in the stomach. FIG. 2 shows the pH relation of the possible binding of phosphate. The effect of various phosphate-gel relations on the kinetics of phosphate binding are shown in FIG. 3.

Further embodiments of the invention and other inventive features are contained in the claims.

DESCRIPTION OF THE DRAWINGS

In the drawings, which illustrate that which is presently regarded as the best mode of carrying out the invention.

FIG. 7 is a diagram showing the oxalate binding capacity of calcium alginate.

DESCRIPTION OF THE PREFERRED EMBODIMENTS

Figure 1:
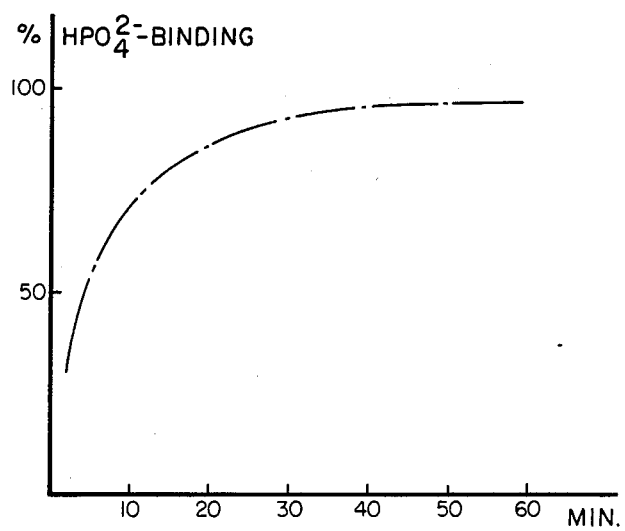
FIG. 1 is a diagram showing the rate of binding of $HPO_4^{2-}$ against time.

The following examples serve to further illustrate the invention.

The following analytical techniques were used in the subsequent examples.

Analytical Determination Techniques (1) Determination of $Ca^{2+}$

For the determination of the calcium content of the calcium alginate, and calcium pectate, respectively, these were dissolved, at pH 8, in 0.1 Mol/EDTA. Excess of EDTA was back-titrated with 0.1 molar $M_gCl_2$ solution at pH 10 (Eriochrome ® Black T mixed-indicator).

(2) Determination of $HPO_4^{2-}$ $HPO_4^{2-}$ was photometrically determined in accordance with the method of Gomorri (G. Gomorri, J. Lab. Clin. Med., 27, p. 955 (1942)). The inorganic phosphate thereby forms phosphorus molybdate in the presence of sodium molybdate. The phosphorus molybdate is converted into colloidal molybdenum blue by reduction with p-methyl-aminophenol sulfate, and the molybdenum blue is determined photometrically.

(3) Determination of Iron ($Fe^{2+}$ plus $Fe^{3+}$) in Calcium Iron Alginate 1 g of calcium iron alginate (IGB-27) is preliminaryly dissolved with 5 ml conc. $HNO_3$, and the total iron is determined as $Fe^{3+}$ by titration with 0.1M Titriplex ® III at pH 2.5 (indicator 5-sulfosalicylic acid; change from blue to colourless).

1 ml of 0.1M Titriplex ® III solution = 5.585 mg iron. 1 g IGB-27 contains 45.2 mg iron.

(4) Determination of Oxalate

The determination of oxalate by titrimetry was carried out using a calibrated 0.02M potassium permanganate solution which had been boiled for 1 hour for stabilization. To 10 ml of the sample (compare Example II) were added 150 ml of bidistilled water and 10 ml of 1+4 diluted, concentrated sulfuric acid, with heating to 75° to 85° C., and titrated with $KMnO_4$ solution until a constant, weak pink colour is obtained.

(5) Determination of Sodium and Potassium

The determinations of K and Na were made after disolution of the gels in EDTA (Titriplex ® III) solution, by flame-photometry or atomic absorption, using standard methods.

EXAMPLE I

PREPARATION OF A CALCIUM ALGINATE GEL (HERE 8%; IGB-11 AND IGB-21)

8 g of alginic acid (Sigma Type III from kelp) were dissolved in 80 ml water under stirring, and the pH was adjusted to 7.4 with 1M NaOH. Alternatively, such a solution can also be prepared by dissolution of sodium alginate (Protanal LFR 5/60 of Protan (company), Norway). The volume of the clear sodium alginate solution is brought to 100 ml by addition of water, stirred for 2 hours at room temperature, and then left for 12 hours. The Na-alginate solution is added in drops, for induration or hardening (bead forming), into a 0.4M $CaCl_2$ solution. During this addition calcium alginate beads are formed having a diameter of approximately 5 mm. These are fully hard in 12 hours at 4° C.

Washing-out of Ca-salts not bound (and other salts, if added): In addition to the calcium ions which are linked to the carboxyl groups of the alginic acid, the Ca-alginate beads prepared in accordance with the foregoing also contain free, washable calcium salts. These can be removed by washing the beads with three times the volume of water (IGB-11, IGB-21).

Drying of the calcium alginate beads: The Ca-alginate beads are freeze-dried. Alternatively, they can be dried for 24 hours at 40° C., or, in order to prevent breaking of the gel structure, only partially dewatered, or treated with additives which maintain the structure.

Contents analysis: (IGB-21): Ca: 160 mg/g; K: 8.2 mg/g; Na: 20 mg/g dry beads.

Doping of calcium alginate gels with $Fe^{2+}$ and other ions: $Fe^{2+}$ and other trace elements can be introduced into calcium alginate by addition of the sodium alginate solution described in the foregoing, for hardening or induration (bead forming), into a 0.4M $CaCl_2$ solution to which $Fe^{2+}$ or other salts as required are added in equal volumes. The required, or desired, respectively, doping can be controlled over side ranges, as well as the consistency of the gel, prior to a subsequent drying. The intensity of the subsequent washing is a determining factor for the adsorptively bound proportion of $Ca^{2+}$, $Fe^{2+}$, and other salts.

PREPARATION OF CALCIUM ALGINATE FOR INTESTINAL PHOSPHATE BINDING

Alginic acid containing 56 to 75% by weight of guluronic acid is obtained, using conventional methods, from the algae Laminaria hyperborea (using either the stems only or the whole plant, but not the leaves only). The alginic acid is neutralized completely with calcium carbonate, and is then thoroughly washed with water and dried to give a calcium alginate containing about 10% by weight of calcium based on the weight of the dried calcium alginate.

This calcium alginate, when tested in the in vitro phosphate binding assay discussed below in Example VII, binds 90–130 mg of phosphate per gram of calcium alginate.

EXAMPLE II

PREPARATION OF A CALCIUM PECTATE GEL (HERE 15%)

15 g pectic acid (Serva No. 31680) are dissolved in 80 ml of water while stirring, and the pH is adjusted to 7.4 by addition of 2M NaOH. The volume of the highly viscous solution is brought to 100 ml by addition of water, and stirred for 2 hours at 60° C. This sodium pectate solution is added in drops, for hardening or induration (bead forming), into 500 ml of a 1M $CaCl_2$ solution which had a pH of 7.4, on addition of 1M NaOH. On addition in drops, calcium pectate beads having a diameter of approximately 5 mm are formed, and these are fully hardened in 15 hours at 4° C. The content of free calcium salts, not linked to carboxyl groups, can be controlled by washing. As described with reference to the calcium alginate gels, the calcium pectate gels can be dried and doped with $Fe^{2+}$, $Fe^{3+}$, and trace salts.

EXAMPLE III

PREPARATION OF IRON CALCIUM ALGINATE GEL (IGB-27)

8 g sodium alginate (Protanal) are dissolved in 80 ml bidistilled water while stirring, and the pH of the solution is brought to 7.4 by addition of 1M NaOH. The volume is brought to 100 ml by the addition of bidistilled water.

The 8% Na-alginate solution is added in drops into 500 ml of a solution with 0.25M $FeCl_2$ and 0.4M $CaCl_2$. On addition, beads of iron calcium alginate are formed which become fully hardened at a temperature of 4° C. in a period of 12 hours.

Washing with water for the removal from the beads of iron and calcium ions not stoichiometrically bound is carried out as described in Example I. The drying is carried out at 40° C. for approximately 24 hours.

Determination of the contents: Ca: 140 mg/g; Fe: 45.2 mg/g; K: 7.8 mg/g; Na: 20 mg/g dry beads.

EXAMPLE IV

PREPARATION OF IRON(III) CALCIUM ALGINATE GEL AT pH 2 (IGB-22)

An 8% sodium alginate solution (prepared as described in Example I) is added in drops into a solution which was prepared by dissolution of 0.125M iron(III) citrate in a heated 0.5M $CaCl_2$ at pH 2.

Induration or hardening, washing, and drying are carried out as described in Example III. The beads have a dark-violet colour.

EXAMPLE V

PREPARATION OF IRON(III) CALCIUM ALGINATE GEL AT pH 6.7 (IGB-23)

66 g iron(III) citrate were dissolved under heating in 100 ml bidistilled water and the pH was adjusted to 6.7 with 1M NaOH. Using this solution, there were prepared, in the usual manner, 2 liters of an 8% Na-alginate solution, which, in accordingly, comprises a 0.125M iron(III) citrate solution. This iron(III) citrate/Na-alginate mixture is added in drops into a 0.4M $CaCl_2$ solution. The resultant dark-violet beads are hardened or indurated, washed, and dried in a manner as described above.

EXAMPLE VI

PREPARATION OF IRON(II) CALCIUM ALGINATE GELS AT pH 2.6 (IGB-25) AND pH 6.8 (IGB-26)

In accordance with Example I one prepares an 8% solution of sodium alginate (100 ml). The hardening or induration (bead forming) solution (500 ml) has the following composition: 0.25M $FeCl_2$, 0.4M $CaCl_2$ and 0.25M L-ascorbic acid (vitamin C).

(a) To 250 ml of the hardening or induration solution with pH 2.6, is added in drops 50 ml of the Na-alginate solution.

(b) To a further 250 ml of the hardening or induration (bead forming) solution (colour: violet), with pH 6.8 by the addition of 1M NaOH, one adds in drops 50 ml of the Na-alginate solution.

After an induration time of 12 hours, the resultant beads are washed and dried (compare Example III), as is custmary. The preparations have the following colours: IGB-25: brownish-yellow; IGB-26: dark-violet.

EXAMPLE VII

Figure 4:
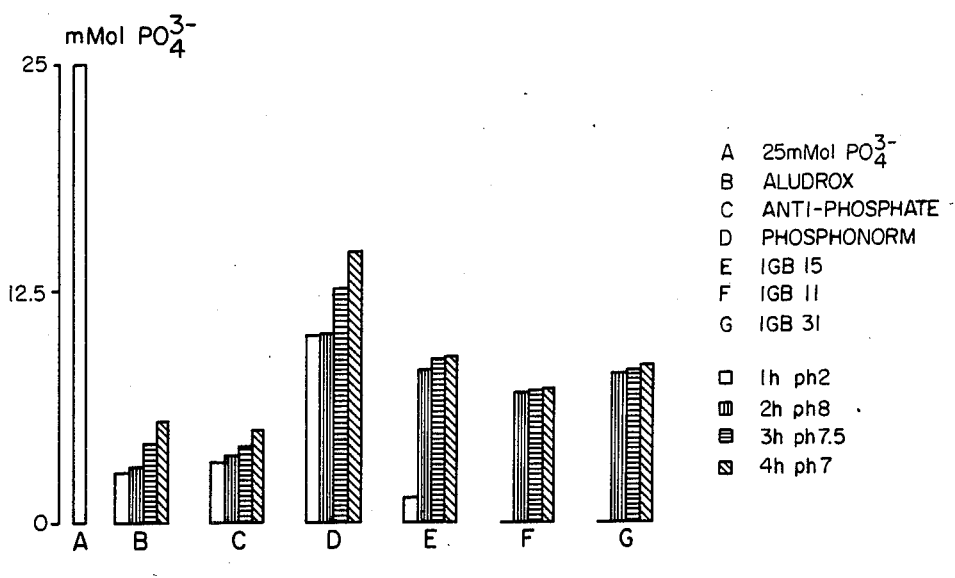
FIG. 4 is a diagram comparing the phosphate binding capacity of various substances.

IN VITRO PHOSPHATE-BINDING CAPACITY OF VARIOUS SUBSTANCES WHICH ARE BASED ON $(AlOH)_3$ AND BASED ON Ca-ALGINATE (FIG. 4)

Respectively 1 tablet or 1 capsule of the phosphate binders based on $Al(OH)_3$ (ALUDROX®, ANTIPHOSPHATE®, and PHOSPHONORM®), as well as 0.45 g of dried, not washed Ca-alginate (IGB-15); dried, washed Ca-alginate (IGB-11); and freshly precipitated $Fe(OH)_3$ (IGB-31), were incubated, on the rollermixer, in 100 ml Iris-buffer with 0.48 g $K_2HPO_4$ (equivalent to 0.2 g phosphate) at pH 2 and 37° C. For one hour to simulate passage through the stomach. (The first sample is for the determination of phosphate). The pH was subsequently adjusted to the value of 8, by the addition of NaOH, a further 0.48 g of $K_2HPO_4$ were added, and incubated for 1 hour (passage throught the intestine). (Then the second sample is taken for the phosphate determination). The pH was adjusted to the value of 7.5, and incubation for 1 hour was carried out. (The third sample is taken.) Further processing at pH 7.0 was analogously carried out. (The fourth sample for the determination of phosphate is taken).

The results are presented in FIG. 4. Only the PHOSPHONORM® was capable of binding more than 50% of the entire initial amount of 25 mM phosphate. The preparation which are based on polyuronic acid, however, are more suitable than the other aluminium-containing preparations.

The in vitro phosphate-binding capacities, per gram, of the phosphate binders ALUDROX ®, ANTIPHOSPHATE ®, PHOSPHONORM ®, and Ca-alginate (IGB-11), are compared in the Table III.

TABLE III

|  | 1 | 2 | 3 | 4 |
|---|---|---|---|---|
| Phosphate Binding | 0.096 g/tabl. | 0.09 g/tabl. | 0.25 g/caps. | 0.155 g |
| Weight (mg) | 580 | 790 | 400 | 450 |
| Phosphate Binding Capacity per Gram | 0.17 g $PO_4^{3-}$ | 0.114 g $PO_4^{3-}$ | 0.625 g $PO_4^{3-}$ | 0.34 g $PO_4^{3-}$ |

1 = ALUDROX ® 1 tablet
2 = ANTIPHOSPHATE ® 1 tablet
3 = PHOSPHONROM ® 1 capsule
4 = Ca-alginate, washed 450 g

EXAMPLE VIII

PHOSPHATE-BINDING CAPACITIES OF VARIOUS ALGINATE PREPARATIONS IN COMPARSION WITH ALUDROX ® AND Fe(OH)$_3$

Respectively 1 g of the following substances were succesively incubated in 200 ml Tris-buffer at various pH values (pH 2; 8; 7.5; and 7), with 0.4 g phosphate, for respectively 1 hour, and subsequently the amount of free phosphate was determined:

IGB-11: Ca-alginate (Sigma), washed,
IGB-15: Ca-alginate (Sigma), not washed,
IGB-21: Ca-alginate (Protan), washed
IGB-22: Iron(III)-Ca-alginate, pH 2 (Example IV),
IGB-23: Iron(III)-Ca-alginate, pH 6.7 (Example V),
IGB-24: Iron(II)-Ca-alginate (no example),
IGB-25: Iron(II)-Ca-alginate, pH 2.6 (Example VI),
IGB-26: Iron(II)-Ca-alginate, pH 6.8 (Example VI),
IGB-27: Iron(II/III)-Ca-alginate (Example III),
IGB-31: freshly precipitated Fe(OH)$_3$,
ALUDROX ®.

Figure 5:
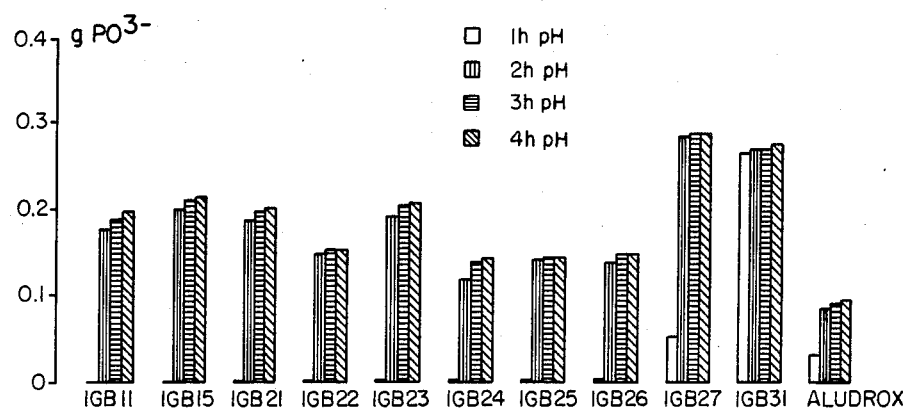
FIG. 5 is a diagram similar to FIG. 4 showing the effect of incubation time and pH.

The results are shown in FIG. 5.

Under acidic conditions (stomach acid), the pure Ca-alginates do not react with phosphate, while the preparation IGB-27 already indicates 16% of its binding capacity. Under neutral, or slightly alkaline conditions (passage through the intestine), IGB-21 can eliminate approximately 50% of the phosphate, and IGB-27 even 73%. Under these conditions ALUDROX ® binds only 24% of the phosphate that is present.

EXAMPLE IX

Figure 6:
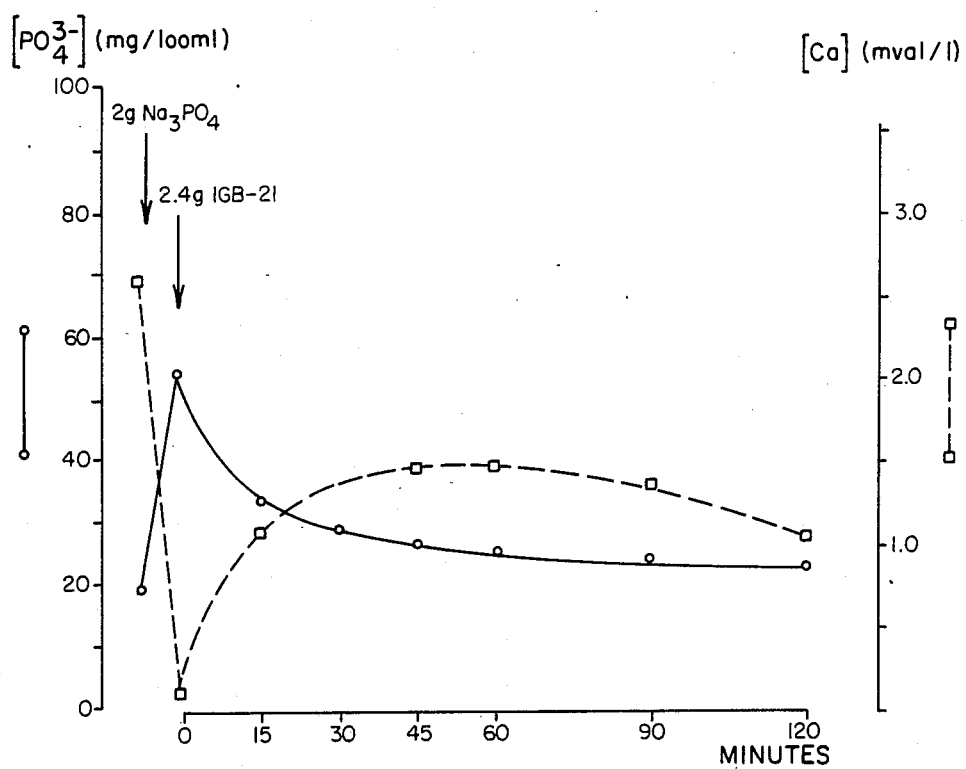
FIG. 6 is a diagram showing elimination of phosphate and behavior of free Ca-concentration.

ELIMINATION OF PHOSPHATE FROM HUMAN DUODENAL FLUID 500 ml of a duodenal fluid (pH 7-8) was enriched with 2 g trisodium phosphate (Na$_2$PO$_4$), and was incubated for 2 hours at 37° C., while stirring, 2.4 g calcium alginate beads (IGB-21). A distinct reduction of phosphate was observed during the initial 45 minutes, and subsequently the lowering of the phosphate concentration was only minor (FIG. 6). After 120 minutes, the phosphate concentration was again near the level of the starting value prior to the loading.

EXAMPLE X

IN VIVO ELIMINATION OF PHOSPHATE 10 patients with chronic kidney failures, of which 9 patients had been given a haemodialysis treatment, and which despite conventional therapy with aluminium hydroxide were showing an excessive level of serum-phosphate (blood phosphate), were treated with calcium alginate beads (IGB-21). The beads had a diameter of 1 to 2 mm and contained 20 mg Na$^+$, 7.8 mg K$^+$, and 160 mg Ca$^+$ per gram dry substance. At an average dosage of 5.4 g Ca-alginate per day, the serum-phosphate values could be reduced over 6 month from 8.5±1.7 mg to 6.1±1.0 mg%, i.e. by 28%, and, accordingly, to an acceptable range. While the K$^+$ values did not change significantly, a lower reduction of the Ca values (10%) was measured (compare Table IV). Side reactions were not observed.

A further advantage was found to reside in the clearly noticable lowering of the constipation associated with the Al(OH)$_3$ therapy.

Analogous investigations were carried out with 5 patients using iron-doped Ca-alginate (IGB-27; with Fe-content 40 mg, Ca-content 140 mg per gram). Similar results as shown in Table IV were obtained.

TABLE IV

AVERAGE VALUES OF THE SERUM CONCENTRATIONS OF PHOSPHATE, CALCIUM, AND POTASSIUM OF 10 PATIENTS WITH CHRONIC KIDNEY FAILURE AFTER TREATMENT WITH AN AVERAGE OF 5.4 g Ca—ALGINATE (IGB-21) PER DAY

|  | Start | 1 | 2 | 3 | 4 | 5 | 6 month |
|---|---|---|---|---|---|---|---|
| Serum Phosphate mg % | 8.5 ±1.7 | 6.0 ±2.2 | 5.5 ±1.1 | 5.6 ±1.5 | 5.8 ±1.2 | 6.0 ±1.3 | 6.1 ±1.0 |
| Serum Calcium mmol/l | 2.35 ±0.23 | 2.44 ±0.21 | 2.41 ±0.16 | 2.46 ±0.14 | 2.35 ±0.10 | 2.29 ±0.16 | 2.15 ±0.13 |
| Dosage of Phosphate Binder g/day |  | 4.6 ±1.8 | 5.0 ±1.9 | 5.5 ±1.9 | 5.6 ±1.8 | 6.0 ±1.7 | 5.4 ±1.8 |
| N | 10 | 10 | 10 | 10 | 7 | 6 | 5 |

EXAMPLE XI

OXALATE-BINDING CAPACITY OF CALCIUM ALGINATE (IGB-21) IN THE PRESENCE OF PHOSPHATE IN CONFORMITY WITH pH AND TIME

For the determination of the oxalate-binding capacity two series of samples were prepared:
(a) 500 g oxalic acid in 190 ml 0.1M Tris-HCl
(b) 500 mg oxalic acid and 960 mg K$_2$HPO$_4$ in 190 ml 0.1M Tris-HCl For representation of the pH conditions in the individual sections of the intestine, within each series samples with the following pH values were prepared: pH 6; 6.5; 7.0; 7.5; and 8.0.

After precise adjustment of the pH with NaOH and HCl, respectively, the solution volume was brought to 200 ml by a buffer solution, and to each sample 1 g calcium alginate (IGB-21) was added. The preparations were incubated in the water bath under light stirring at 37° C., and 12 ml of aliquot were taken after 10, 30, 60, and 120 minutes, respectively. Ca-oxalate which had formed was removed by centrifuging, and from the remainder respectively 10 ml were titrated to free oxalate using $KMnO_4$ solution (see determination techniques).

The results are shown in FIG. 7. For comparison there are shown the amounts of oxalate removed at pH 7.0 without phosphate. Generally, the oxalate-binding capacity of Ca-alginate (IGB-21) is greatest at incubation periods of from 30 minutes upwards, at pH 6.0, and it is then decreasing up to pH 7.5. at pH 7, 1 g Ca-alginate binds approximately 165 mg oxalate. In the presence of phosphate, the oxalate-binding capacity of IGB-21 is reduced by approximately 20% when the reaction time is of from 30 minutes or more.

Further details of the drawings are discussed in the following:

FIG. 1—kinetics of the binding of $HPO_4^{2-}$ by calcium alginate gel (8%). Calcium alginate gel (8%, washed 5 times), containing only calcium ions linked to carboxyl groups, were incubated, on the roller-mixer, with an excess, with 5.5 mM $HPO_4^{2-}$ in Tris-HCl buffer (pH 8; 0.2M), at 37° C. Samples were withdrawn at different times for determination, after centrifuging, of the $HPO_4^{2-}$ concentration (compare also FIG. 3).

Figure 2:
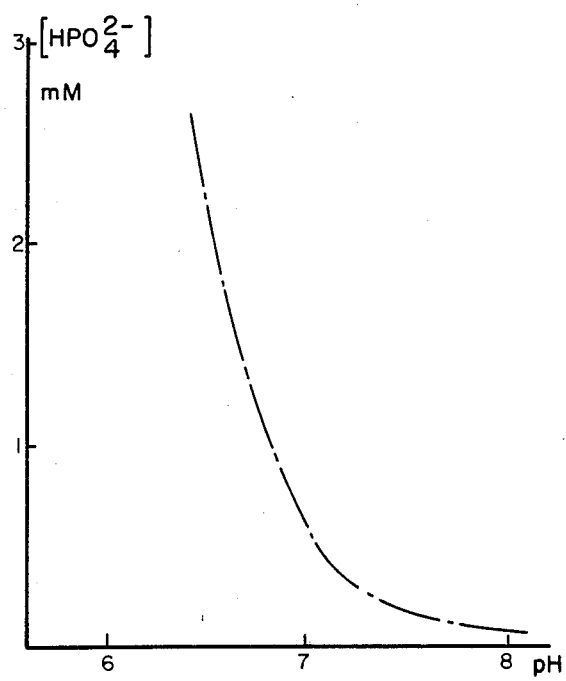
FIG. 2 is a diagram showing the effect of free $HPO_4^{2-}$ in relation to pH.

FIG. 2—Maximum concentration of unbound $HPO_4^{2-}$ in conformity with the pH. Calcium alginate ((%) was incubated for 30 minutes, respectively, with an excess of 5.5 mM $HPO_4^{2-}$ in Tris-HCl buffer solution (0.2M) at 37° C. in the roller-mixer, and at various pH values. After centrifuging the concentration of $HPO_4^{2-}$ of the residues was determined.

Figure 3:
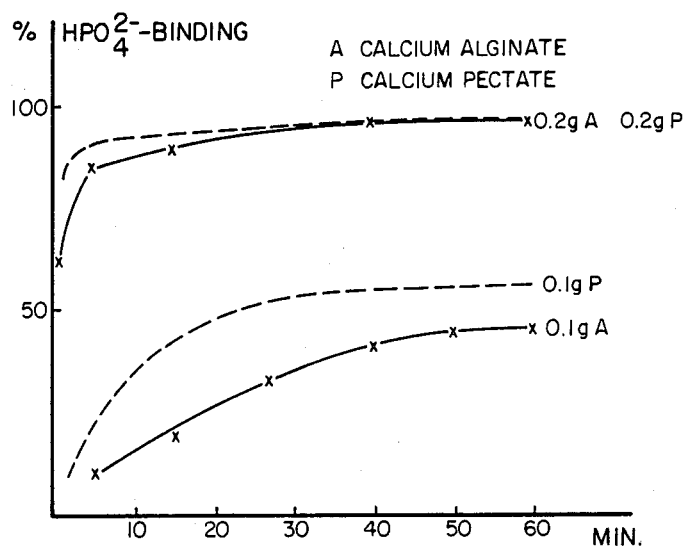
FIG. 3 is a diagram similar to FIG. 1

FIG. 3—Kintetics of the binding of $HPO_4^{2-}$ using calcium alginate (20%) and calcium pectate (15%). Various amounts of calcium alginate gel (20%) and calcium pectate gel (15%), each doped with 1M $CaCl_2$ solution (pH 7.4), were incubated in the roller-mixer at 37° C. with 10 ml of 5.5 mM $HPO_4^{2-}$ in Tris-HCl buffer solution (pH 8, 0.2M). Samples were taken at different times and the concentration of $HPO_4^{2-}$ was determined in these.

FIG. 4—In vitro phosphate-binding capacity of various substances on $Al(OH)_3$ basis (B,C, and D), Ca-alginate basis (E and F), and of $Fe(OH)_3$ (G) (compare Example VII). The column A presents the total amount of starting phosphate (25 mM).

FIG. 5—Phosphate-binding capacity of various phosphate binders in vitro (per gram substance) in conformity with the incubation period under various pH conditions (compare Example 8). Respectively, 0.4 g phosphate were initially present.

FIG. 6—Elimination of phosphate by 2.4 g Ca-alginate (IGB-21) from human duodenal fluid enriched with 2 g $Na_3PO_4$ (compare Example IX). The behavior of the free Ca-concentration over the period of the tests of 120 minutes is also plotted.

FIG. 7—Oxalate-binding capacity of calcium alginate (IGB-21) at various pH values in conformity with the incubation period, in the presence of phosphate (plain, open columns) and in the absence of phosphate, respectively, (dotted columns). Compare also Example XI.

PREPARATION OF SOFT GELATIN CAPSULES OF CALCIUM ALGINATE

Soft gelatin capsules containing the desired high amounts of calcium alginate are prepared in the following way:

(a) Soft gelatin capsule with hydrophobic filling material 100 kg of gelatin is mixed with 1.5 kg of glycerol and 80 kg of water (gelatin mass). 10 kg of medium chain triglycerides and 2 kg of soja lecithin are mixed, followed by addition of 50 kg of the preferred calcium alginate (prepared from alginic acid obtained from *Laminaria hyperborea;* see Example I) with thorough mixing (filling material).

From the above gelatin mass and the above filling material are prepared about 50.000 soft gelatin capsules using conventional methods, each capsule containing about 1 g of the pharmaceutically active ingredient calcium alginate.

(b) Soft gelatin capsule with hydrophilic filling material 100 kg of gelatin is mixed with 1.5 kg of glycerol and 80 kg of water (gelatin mass). 10 kg of polyethylenglycol and 50 kg of the above-described calcium alginate are thoroughly mixed (filling material).

From the above gelatin mass and the above filling material are prepared 50.000 soft gelatin capsules using conventional methods, each capsule containing about 1 g of the pharmaceutically active ingredient calcium alginate.

Reference in this disclosure to details of the specific embodiments is not intended to restrict the scope of the appended claims, which themselves recite those features regarded as essential to the invention.

We claim:

1. An orally administerable pharmaceutical composition for use in the treatment of hyperphosphateaemia and for preventing the formation of phosphate- and oxalate-containing kidney stones which comprises as the principal active ingredient a therapeutically effective amount of a salt of a natural polymeric, anionic carboxylic acid in which the cation of said salt is selected from (a) calcium and (b) a mixture of calcium with at least one other cation selected from iron and trace elements, the total of cation in said salt being present in an amount equivalent to 0.5–5.0 of the stoichiometric amount, and the amounts of calcium and other cation being present in said mixture in amounts equivalent to 0.45–4.95 and 0.05–2–5, respectively, of the stoichiometric amount, said principal active ingredient being combined with a pharmaceutically acceptable carrier in the form of beads, tablets, capsules, powders, dragees or pills.

2. A pharmaceutical composition according to claim 1 in which the carboxylic acid is selected from polymannuronic acid, polygalacturonic acid, polyguluronic acid and mixtures thereof.

3. A pharmaceutical composition according to claim 2 in which the principal active ingredient is selected from calcium alginate and calcium pectate.

4. A pharmaceutical composition according to claim 3 particularly adapted for treating hyperphosphateaemia and for preventing the formation of phosphate-containing kidney stones in which the principal active ingredient is calcium alginate in which the calcium is present in an amount equivalent to 0.8-1.1 of the stoichiometric amount thereby providing a calcium content of 8.5-11.5% by wt. calcium based on the dry weight of the calcium alginate, said calcium alginate having been prepared from an alginic acid comprising 56-75% by wt. of guluronic acid and 25-44% by wt. of mannuronic acid obtained from the algae *Laminaria hyperborea.*

5. A pharmaceutical composition according to claim 4 which is in the form of a soft gelatin capsule comprising 0.5-1.2 grs. of said principal active ingredient.

6. A pharmaceutical composition according to claim 2 in which the principal active ingredient is selected from calcium-iron alginate and calcium-iron pectate in which the calcium and iron are present in amounts equivalent to 1.0-2.0 and 0.3-0.6, respectively, of the stochiometric amount.

7. A method for treating hyperphosphateaemia and for preventing the formation of phosphate- and oxalate-containing kidney stones in humans which comprises orally administering to a person in need thereof a pharmaceutical composition according to claim 1.

8. A method for treating hyperphosphateaemia and for preventing the formation of phosphate- and oxalate-containing kidney stones in humans which comprises orally administering to a person in need thereof a pharmaceutical composition according to claim 2.

9. A method for treating hyperphosphateaemia and for preventing the formation of phosphate- and oxalate-containing kidney stones in humans which comprises orally administering to a person in need thereof a pharmaceutical composition according to claim 3.

10. A method for treating hyperphospateaemia and for preventing the formation of phosphate-containing kidney stones in humans which comprises orally administering to a person in need thereof a pharmaceutical composition according to claim 4.

11. A method for treating hyperphosphateaemia and for preventing the formation of phosphate-containing kidney stones in humans which comprises orally administering to a person in need thereof a pharmaceutical composition according to claim 5.

12. A method for treating hyperphospateaeima and for preventing the formation of phosphate- and oxalate-containing kidney stones in humans which comprises orally administering to a person in need thereof a pharmaceutical composition according to claim 6.

* * * * *